(12) United States Patent
Peery (10) Patent No.: US 9,744,020 B1
(45) Date of Patent: Aug. 29, 2017

(54) MESH FOR HIATAL HERNIA REPAIR AND DEPLOYMENT DEVICE

(71) Applicant: Sanford Health, Sioux Falls, SD (US)

(72) Inventor: Curtis Peery, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 0 days.

(21) Appl. No.: 15/430,092

(22) Filed: Feb. 10, 2017

Related U.S. Application Data (60) Provisional application No. 62/294,504, filed on Feb. 12, 2016.

(51) Int. Cl.
*A61B 17/08* (2006.01)
*A61F 2/00* (2006.01)
(Continued)

(52) U.S. Cl.
CPC ...... *A61F 2/0063* (2013.01); *A61B 17/00234* (2013.01); *A61B 17/29* (2013.01); *A61B 34/30* (2016.02); *A61B 2017/00473* (2013.01); *A61B 2017/00477* (2013.01); *A61B 2017/00876* (2013.01); *A61B 2017/2926* (2013.01); *A61B 2017/2946* (2013.01); *A61F 2002/0068* (2013.01); *A61F 2002/0072* (2013.01); *A61F 2210/0076* (2013.01); *A61F 2220/0008* (2013.01); *A61F 2220/0016* (2013.01); *A61F 2250/0067* (2013.01)

(58) Field of Classification Search
CPC ...... A61F 2002/0072; A61F 2220/0008; A61F 2220/0016; A61B 17/29; A61B 2017/2926; A61B 2017/2927; A61B 2017/2939
See application file for complete search history.

(56) References Cited

U.S. PATENT DOCUMENTS 6,773,440 B2 * 8/2004 Gannoe ............ A61B 17/00234
606/142
6,872,227 B2 * 3/2005 Sump ............... A61B 17/29
606/151
(Continued)

FOREIGN PATENT DOCUMENTS

EP 2799026 A2 11/2014
WO 2015/157459 A1 10/2015

*Primary Examiner* — Jonathan Miles
(74) *Attorney, Agent, or Firm* — McDonnell Boehnen Hulbert & Berghoff LLP (57) ABSTRACT

The present disclosure provides a deployment device that includes (a) an elongate shaft having a first end and a second end, (b) a grasping assembly coupled to the first end of the elongate shaft, where the grasping assembly includes a first jaw and a second jaw rotatable with respect to the elongate shaft, where the grasping assembly is configured to accept a wound closure device between the first jaw and the second jaw, where the wound closure device comprises at least two fixation components connected to and extending therethrough, where each of the first jaw and the second jaw include at least one coupling element configured to be removably coupled to a respective fixation component when the wound closure device is coupled to the grasping assembly, and (c) an actuator coupled to the second end of the elongate shaft, where the actuator is configured to move the grasping assembly between an open position and a closed position.

18 Claims, 7 Drawing Sheets

(51) Int. Cl.
*A61B 17/29* (2006.01)
*A61B 17/00* (2006.01)
*A61B 34/30* (2016.01)

(56) References Cited

U.S. PATENT DOCUMENTS

| | | |
|---|---|---|
| 2002/0065534 A1 | 5/2002 | Hermann |
| 2003/0004580 A1* | 1/2003 | Sump ............... A61B 17/29 623/23.72 |
| 2004/0006351 A1* | 1/2004 | Gannoe ........... A61B 17/00234 606/139 |
| 2004/0162568 A1* | 8/2004 | Saadat ............... A61B 1/00135 606/139 |
| 2005/0192633 A1* | 9/2005 | Montpetit .......... A61B 17/0469 606/232 |
| 2005/0267529 A1* | 12/2005 | Crockett ......... A61B 17/00234 606/215 |
| 2006/0041243 A1* | 2/2006 | Nayak ............... A61B 17/0206 604/506 |
| 2008/0140095 A1 | 6/2008 | Cropper |
| 2009/0054732 A1* | 2/2009 | Markham ............ A61B 17/29 600/127 |
| 2011/0190809 A1 | 8/2011 | Mohan |

\* cited by examiner

MESH FOR HIATAL HERNIA REPAIR AND DEPLOYMENT DEVICE

RELATED APPLICATIONS

This application claims the benefit of priority to U.S. Provisional Application No. 62/294,504 entitled "Mesh for Hiatal Hernia Repair and Deployment Device," filed on Feb. 12, 2016, the contents of which are hereby incorporated by reference in their entirety.

BACKGROUND THE INVENTION

The diaphragm is the muscular wall separating the thoracic cavity from the abdominal cavity. The hiatus is a hole in the diaphragm through which the esophagus passes. When an internal tissue expands into an area it does not belong, it is known as a hernia. In a hiatal hernia, the stomach (which is normally in the abdominal cavity) extrudes through the hiatus and into the thoracic cavity. There are two types of hiatal hernias: (i) a sliding hiatal hernia, and (ii) a paraesophageal hiatal hernia. In a sliding hernia, the esophagus and stomach both move cranially through the hiatus. In a paraesophageal hernia, the stomach moves cranially through the hiatus relative to the esophagus. This movement can cause pinching or strangulation of the stomach which can cause localized ischemia which can be life threatening.

A hiatal hernia is caused by either a naturally large hiatus or increased abdominal pressure from pregnancy or obesity. In one example, a hiatal hernia can be diagnosed via x-ray with barium swallow, which allows visualization of the esophagus. In another example, a hiatal hernia can be diagnosed with endoscopy. When a physician believes that the stomach is at risk of constriction or strangulation, the hiatal hernia needs to be surgically repaired. The procedure to repair a hiatal hernia is referred to as reducing the hernia, which essentially entails putting the stomach back where it belongs. Open surgery is very invasive in this setting and should be avoided. Laparoscopic approaches allow for a 'minimally invasive' option. In the laparoscopic approach, a laparoscope is inserted through a 5-10 mm incision, and allows the surgeon to visualize the hernia while also repairing it. Advantages of laparoscopic surgery include smaller incision, less risk of infection, less pain and scarring, and a quicker recovery.

In paraesophageal hernia repair, a left side transthoracic laparoscopic access is performed. The hernia sac is dissected off the intrathoracic structures of the mediastinum. Once the sac is mobilized, it is excised down to the anterior wall of the esophagus and around the gastropharangeal junction. The esophagus is mobilized so that approximately 3 cm of the distal esophagus lies in the abdomen. Then the enlarged diaphragmic hiatus is closed primarily with suture for tension repair. The sutures are used to approximate the cura or pillars of the diaphragm. While such suturing is effective, it is time consuming and manually challenging. If this suturing step could be eliminated, it would greatly improve efficiencies in the operating room.

Laparoscopic surgery is another method to perform surgery in a minimally invasive way. A laparoscope is used where a camera is attached to a rod and passed into the abdominal cavity, allowing for 2D visualization. The endoscope is passed through a trocar. The abdominal cavity is insufflated with carbon dioxide. Through other incision sites various tools can be passed. The surgeon is in the field directly manipulating the tools, while a technician holds the endoscope. While this approach is minimally invasive with minimal cost requirements, the surgeon has limited range of motion at the surgical site resulting in a loss of dexterity. The surgeon also has a poor depth perception. Also, the tool endpoints move in the opposite direction to the surgeon's hands due to the pivot point of the device, making laparoscopic surgery a non-intuitive motor skill that is difficult to learn.

Robotic surgery is another method to perform surgery using very small tools attached to robotic arms. The surgeon controls the robotic arm with a computer, where she sits at the computer station away from the field and directs the movements of the robot with small surgical tools being attached to the arms of the robot. Small incisions are made to pass the three trocars into the abdominal cavity through which the endoscope (camera) allows the surgeon to see enlarged 3D images within the abdominal cavity of the patient. The robot matches the surgeon's hand movements to perform the procedure using the tiny movements. The 3D visualization and intuitive movement of the robotic arms make hiatal hernia more manageable. However, such a system comes with a substantial capital investment. As such, an improved device for repairing a hiatal hernia may be desirable.

SUMMARY OF THE INVENTION

The present invention will eliminate suture steps in hiatal hernia repair, enabling a less costly laparoscopic technique, while also speeding up robotic surgeries in the setting of hiatal hernia repair. The present invention includes a deployment system for use with laparoscopic or robotic surgery in repair of hiatal hernias. The device actuates to bring the crus of the diaphragm into apposition and affix them in such a way as to close the hiatus around the esophagus with a biocompatible material that has affixed fixation components which pass through the diaphragm and serve as anchors. The device saves surgical time by eliminating the suturing of the crus of the diaphragm.

In particular, in one aspect, the present disclosure provides a deployment device that includes (a) an elongate shaft having a first end and a second end, (b) a grasping assembly coupled to the first end of the elongate shaft, where the grasping assembly includes a first jaw and a second jaw rotatable with respect to the elongate shaft, where the grasping assembly is configured to accept a wound closure device between the first jaw and the second jaw, where the wound closure device comprises at least two fixation components connected to and extending therethrough, where each of the first jaw and the second jaw include at least one coupling element configured to be removably coupled to a respective fixation component when the wound closure device is coupled to the grasping assembly, and (c) an actuator coupled to the second end of the elongate shaft, wherein the actuator is configured to move the grasping assembly between an open position and a closed position.

In another aspect, the present disclosure provides a method of closing a wound in a tissue, the method includes (a) bringing a wound closure device coupled to a deployment device adjacent to the tissue surface, where the wound closure device includes (i) at least two fixation components connected to and extending therethrough, and where the deployment device includes (i) an elongate shaft having a first end and a second end, (ii) a grasping assembly coupled to the first end of the elongate shaft, where the grasping assembling includes a first jaw and a second jaw rotatable with respect to the elongate, where the grasping assembly is configured to accept a wound closure device between the first jaw and the second jaw, and (iii) an actuator coupled to the second end of the elongate shaft, where the actuator is configured to move the grasping assembly between an open position and a closed position, (b) with the grasping assembly in the open position, bringing the wound closure device into abutment with the tissue surface, and (c) bringing the grasping assembly into the closed position around a portion of the tissue surface such that the at least two fixation components pierce the tissue surface, thereby affixing the wound closure device to the tissue surface.

These as well as other aspects, advantages, and alternatives, will become apparent to those of ordinary skill in the art by reading the following detailed description, with reference where appropriate to the accompanying drawings.

DETAILED DESCRIPTION OF THE INVENTION

Exemplary devices and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means+/−5%.

As used herein, "mediastinum" means the mass of tissues and organs separating the sternum in front and the vertebral column in back, containing the heart and its large vessels, trachea, esophagus, thymus, lymph nodes, and other structures and tissues.

As used herein, "excise" means to remove by cutting.

As used herein, "blunt dissection" means a separation of tissues along natural lines of cleavage by means of blunt instrument or finger.

As used herein, "hiatal hernia" means a protrusion of a portion of the stomach through the esophageal hiatus of the diaphragm.

As used herein, "hernia" means an abnormal protrusion of part of an organ or tissue through the structures normally containing the organ or tissue.

As used herein, "esophageal hiatus" means the opening in the diaphragm for the passage of the esophagus and the vagus nerve.

As used herein, "esophagus" means the musculomembranous passage extending from the pharynx to the stomach, 25 cm to 30 cm long in an adult, consisting of an outer fibrous coat, a muscular layer, a submucous layer and an inner mucous membrane.

As used herein, "crus of the diaphragm" means the tendinous structures that extend inferiorly from the diaphragm to attach to the vertebral column. The crus of the diaphragm forms a tether for muscular contraction and runs along the left and right sides of the esophagus.

As used herein, "diaphragm" means a sheet of skeletal muscle that extends across the bottom of the rib cage. The diaphragm separates the thoracic cavity from the abdominal cavity and performs the function of respiration.

As used herein, "stomach" means a muscular hollow dilated part of the digestive system located between the esophagus and small intestine. The stomach secretes protein digesting enzymes called proteases and strong acids to aid in food digestion. Through smooth muscle contortions (i.e., "segmentation") the esophagus delivers food to the stomach before the food is sent to the small intestines as chime.

As used herein, "strangulated hiatal hernia" means a paraesophageal hiatal hernia that cuts off blood supply to the hernia. Without blood and oxygen supply the strangulated tissues begin to die. Such a condition may be life threatening.

As used herein, "laparoscopic surgery" means minimally invasive surgery performed through two small incisions. Such a procedure includes a laparoscope passed through a 10 mm cannula or trocar. The abdominal cavity is inflated with $CO_2$ to create room to work. A tool is placed through a second incision and is used to manipulate tissues under 2D visualization.

As used herein, "laparotomy" means a large surgical incision into the abdominal cavity for diagnosis or in preparation for surgery.

As used herein, "endoscope" means a slender tubular instrument, such as an athroscope or laparoscope, that is inserted into a body cavity or body part for the purpose of visual examination, diagnosis or surgical treatment.

As used herein, "trocar" means a sharp pointed surgical instrument used with a cannula to puncture a body cavity for fluid aspiration As used herein, "surgical mesh" means loosely woven sheet which is used as either a permanent or temporary support for a midline incision upon closure. A surgical mesh can be created from inorganic, organic, biological materials or a combination thereof.

As used herein, "fixation component" means a single use device used to fix a biocompatible material of a wound closure device to the soft tissue, such as the crus of the diaphragm.

As used herein, "biocompatible material" means any suitable biocompatible material, either synthetic or biologic, such as titanium, nitinol, polypropylene, polyethylene terephthalate (PET), Poly-4-hydroxybutyrate (P4HB) and Polytetrafluoroethylene (PTFE).

Figures 1, 2A:
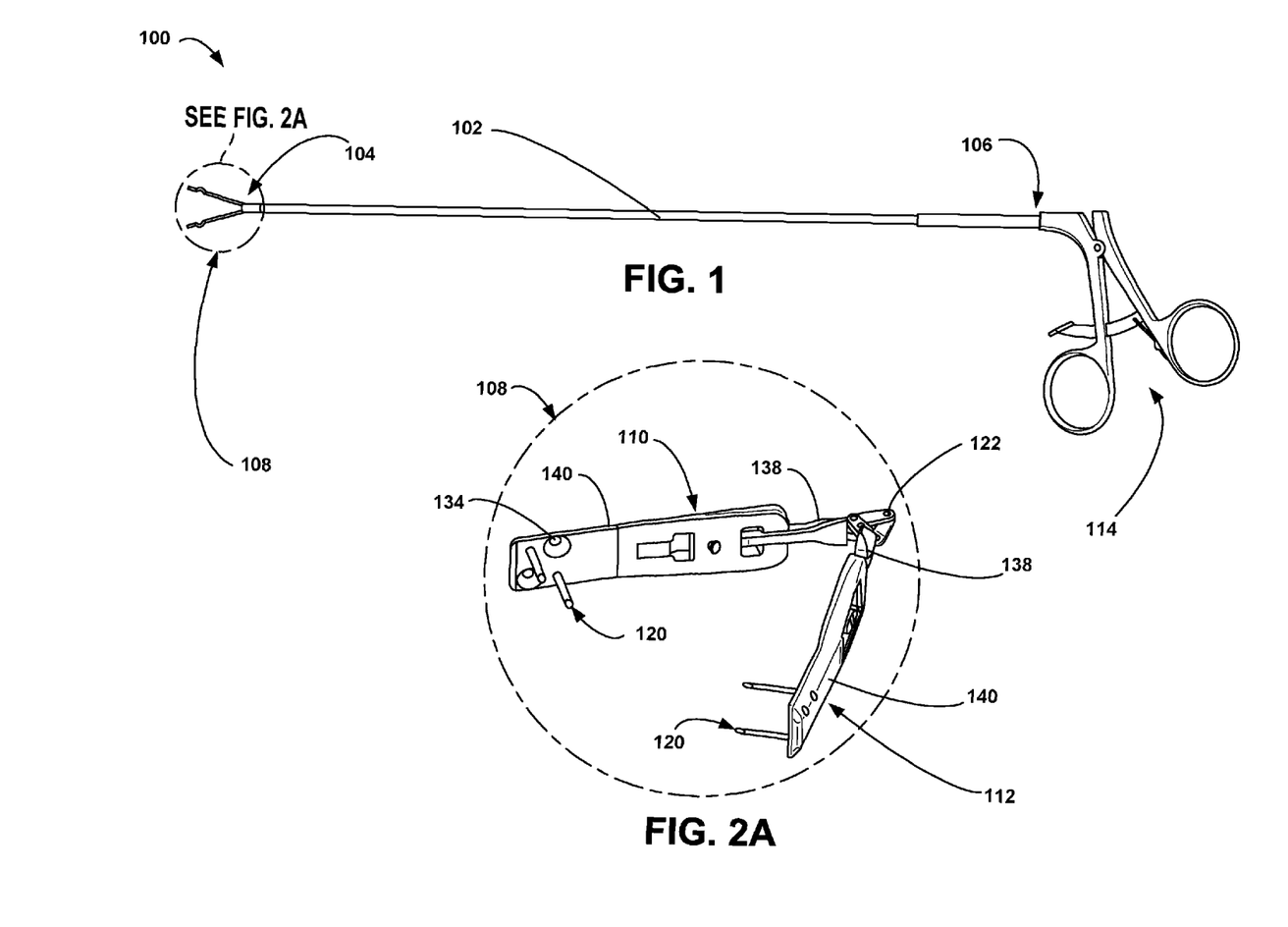
FIG. 1 is a perspective view of a deployment device, according to an example embodiment.
FIG. 2A is a perspective view of an example grasping assembly of the deployment device of FIG. 1 in an open position, according to an example embodiment.
Figures 2B, 2C:
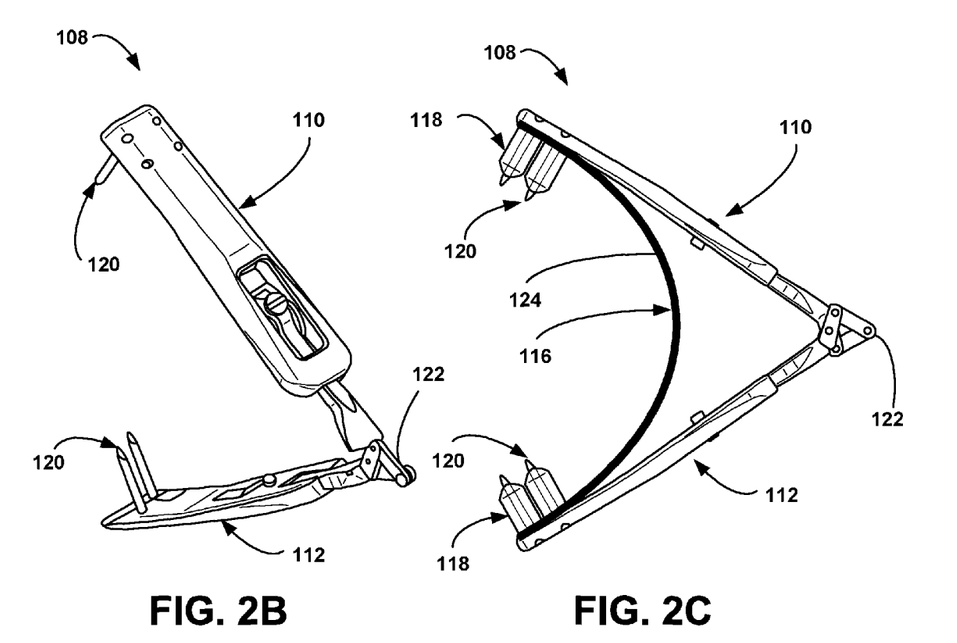
FIG. 2B is another perspective view of an example grasping assembly of the deployment device of FIG. 1 in an open position, according to an example embodiment.
FIG. 2C is a side view of an example grasping assembly of the deployment device of FIG. 1 in an open position with a wound closure device attached thereto, according to an example embodiment.
Figure 2D:
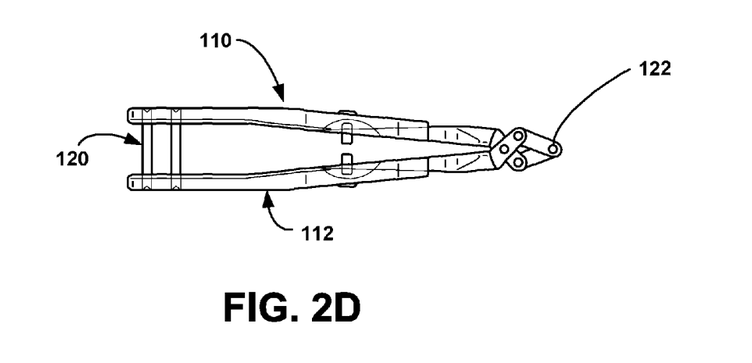
FIG. 2D is a side view of an example grasping assembly of the deployment device of FIG. 1 in a closed position, according to an example embodiment.

A deployment device for positioning and affixing a wound closure device within a body is provided herein. In particular, FIG. 1 illustrates a deployment device 100, according to an example embodiment. As shown in FIG. 1, the deployment device 100 includes an elongate shaft 102 having a first end 104 and a second end 106. The deployment device 100 also includes a grasping assembly 108 coupled to the first end 104 of the elongate shaft 102. As shown in FIG. 2, the grasping assembly 108 includes a first jaw 110 and a second jaw 112 rotatable with respect to the elongate shaft 102. The deployment device 100 also includes an actuator 114 coupled to the second end 106 of the elongate shaft 102. The actuator 114 is configured to move the grasping assembly 108 between an open position (shown in FIGS. 2A-2C) and a closed position (shown in FIG. 2D).

In use, the grasping assembly 108 is configured to accept a wound closure device 116 between the first jaw 110 and the second jaw 112, as shown in FIG. 2C. The wound closure device 116 may include at least two fixation components 118 connected to and extending through the wound closure device 116 such that a flange 125 of each fixation component 118 resides on one side of the wound closure device 116 and a pointed tip 127 of each fixation component 118 extends from the other side of the wound closure device 116. Each of the first jaw 110 and the second jaw 112 include at least one coupling element 120 configured to be removably coupled to a respective fixation component 118 when the wound closure device 116 is coupled to the grasping assembly 108. As described in more detail below, in practice, the coupling element 120 helps hold the wound closure device 116 in position on the first jaw 110 of the grasping assembly 108 prior to and during placement of the wound closure device 116 in vivo.

As discussed above, the grasping assembly 108 includes a first jaw 110 and a second jaw 112. In one example, the second jaw 112 is rotatable with respect to the first jaw 110. In some cases, the first jaw 110 could be stationary while the second jaw 112 is rotatable, and vice versa. In other cases, the first jaw 110 may be rotated independently of the second jaw 112, and vice versa. For instance, the first jaw 110 could be coupled to a first wire that is movable with one finger (or thumb) and the second jaw 112 coupled to a second wire that is movable with a different finger (or thumb). In further embodiments, the first jaw 110 and the second jaw 112 are both rotatable with respect to the other.

As discussed above, the grasping assembly 108 is configured to accept a wound closure device 116 arranged between the first jaw 110 and the second jaw 112. Accordingly, the grasping assembly 108 may be sized and shaped to accommodate the size, shape and implantation characteristics of one or more wound closure devices 116 and the particular requirements or limitations of the surgical procedure. In one example, the wound closure device 116 may be deformed into a crescent shape to be received between the two jaws 110, 112 of the grasping assembly 116, as shown in FIG. 2C. The jaws 110, 112 may be essentially planar, and configured to connect at a pivot point 122. In one example shown in FIG. 2D, a first portion of each of the jaws 110, 112 may be arranged parallel to each other in the closed position to provide clearance room for the coupling element(s) 120 and a second portion of each of the jaws 110, 112 may be angled from the first portion towards the pivot 122 point.

The wound closure device 116 may include any device capable of closing or repairing a tissue wound, for example, as the result of an injury, defect or a surgical procedure. Generally, the wound closure device 116 may take the place of or be used in combination with sutures, staples or other common closure devices. In addition, the wound closure device 116 may serve as a scaffolding, a replacement for, or to strengthen an affected tissue surface, such as the diaphragm. For example, the wound closure device 116 may be used in abdominal surgery, such as in the repair of a hiatal hernia. The wound closure device 116 may be made of any biocompatible material, including bioinert materials, suitable for introduction into a living body. Generally, the wound closure device 116 is configured to be brought into abutment with a tissue surface requiring repair or closure. For example, the wound closure device 116 may be fabricated from a woven type material, such as a mesh 124 (described further below), or a solid material. In either case, the wound closure device 116 may include a number of pores or holes to allow for tissue ingrowth and the passage of fluid. Further, the wound closure device 116, which may be provided as a mesh, may also be capable of eluting one or more drugs or agents into the tissue. One or more drugs or agents may be coated on or impregnated in (e.g., loaded in the pores of the mesh) the closure apparatus material.

The shape, size, thickness and other characteristics of the wound closure device 116 may be selected based on the size, shape and type of wound to be closed, the needs or limitations of the patient, or surgeon preference, among other things. In some examples, the wound closure device 116 may be provided in a predetermined shape. Alternatively, the wound closure device 116 may be provided as a sheet of material capable of being cut to size by a surgeon. The mesh may be bioabsorbable, partially bioabsorbable, or non-bioabsorbable (i.e., permanent) and made of any suitable biocompatible material, either synthetic or biologic, such as titanium, nitinol, polypropylene, polyethylene terephthalate (PET), Poly-4-hydroxybutyrate (P4HB) and Polytetrafluoroethylene (PTFE). Additionally, the mesh may be flexible and, in some cases, stretchable to conform to the shape of a tissue surface. Composite meshes, or multilayer meshes, combining different materials may also be used. The pore and filament size of the mesh may be customized or selected based on the needs of the patient or surgeon preference. A mesh having a higher porosity may promote faster and more extensive tissue integration. For example, in some cases, a thin filament, large pore construction mesh may be selected.

In some embodiments, the mesh is a microreplicated mesh. A "microreplicated" material may include any material that is self-fixating and/or increases friction so as to prevent sliding of the wound closure device 116 along the tissue surface. An exemplary "microreplicated" mesh includes a mesh having a plurality of microgrips made of monofilament polylactic acid ("PLA"). Reducing or prohibiting movement between the wound closure device 116 and the tissue surface may encourage pervasive and faster tissue ingrowth into the wound closure device 116, thereby speeding wound healing and recovery of the patient. Further, the microreplicated surface may provide stability to the wound area, further reducing the occurrence of hiatal hernia. The microreplicated mesh may, in one example, be designed such that the mesh material itself forms a microreplicated surface and there are no added components to the mesh. In another embodiment, the microreplicated mesh is constructed from a separate microreplicated material that is printed or onlayed onto the mesh surface. The replicated material can range in size and form. A multilayer mesh may include a composite mesh having more than one layer of the same or different materials. In one example, the multilayer mesh may include a typical surgical mesh with a layer of microreplicated material coated, applied or laminated thereto. Moreover, the multilayer mesh may comprise some bioabsorbable and some non-bioabsorbable materials. The mesh may be used for both contaminated and non-contaminated wounds.

Each jaw 110, 112 of the grasping assembly 108 includes at least one coupling element 120 configured to releasably couple with a fixation component 118 connected to the wound closure device 116. The coupling element 120 may comprise any structure capable of releasably coupling the fixation components 118 of the wound closure device 116 to the first and second jaws 110, 112 of the deployment device 108. As shown in FIGS. 2A-2D, and as will be described further herein, the coupling element 120 may comprise at least one pin configured to receive a fixation component 118 thereon. The coupling element 120 may also comprise a structure for physically mating with the head or eyelet of the fixation component 118, such as a flange. The number and size of the coupling elements 120 may affect the size and shape of the jaws 110, 112 of the grasping assembly 108. In operation, the coupling element 120 and the tension of the wound closure device 116 (similar to that of a compressed spring) may act to hold the wound closure device 116 within the grasping assembly 108.

Figure 3A:
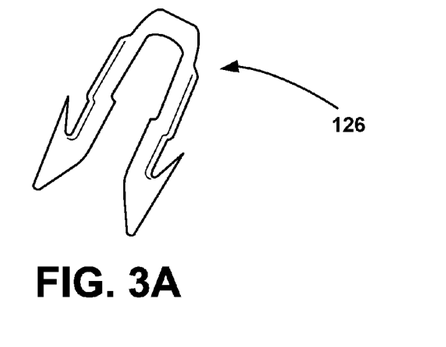
FIG. 3A is a perspective view of an example fixation component, according to an example embodiment.
Figure 3B:
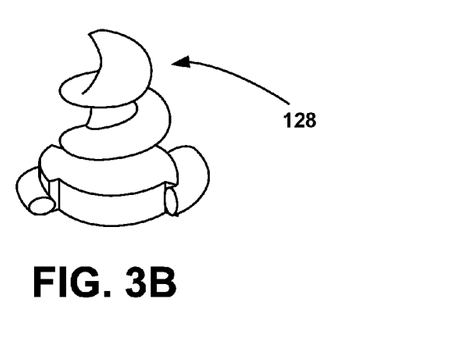
FIG. 3B is a perspective view of an example fixation component, according to an example embodiment.
Figure 3C:
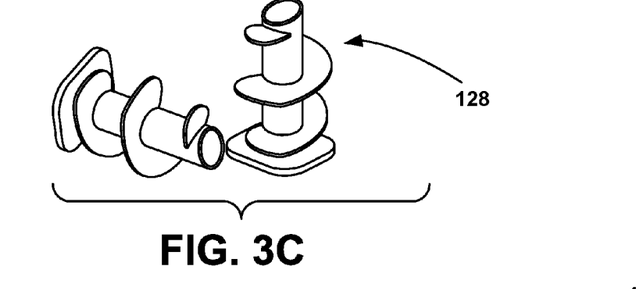
FIG. 3C is a perspective view of an example fixation component, according to an example embodiment.
Figure 3D:
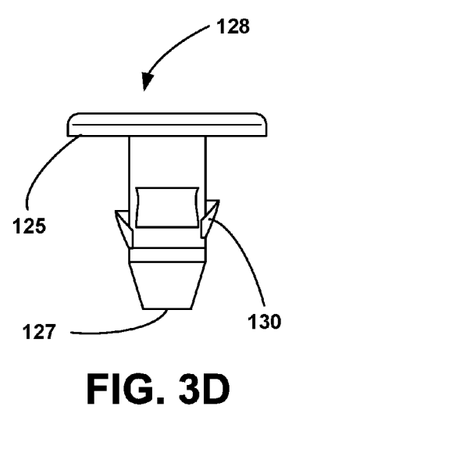
FIG. 3D is a side view of an example fixation component, according to an example embodiment.
Figure 3E:
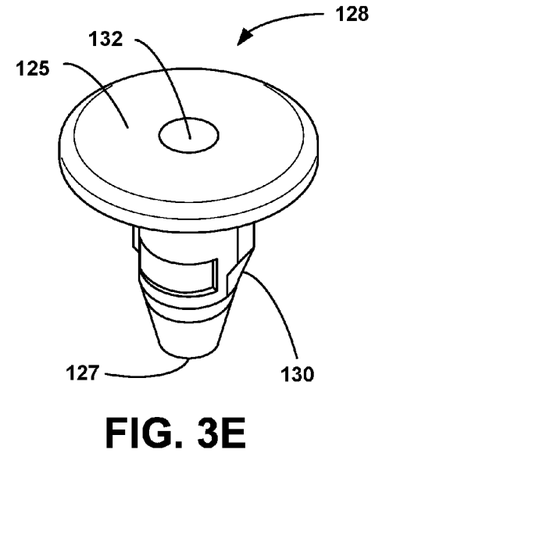
FIG. 3E is a perspective view of an example fixation component, according to an example embodiment.
Figure 4:
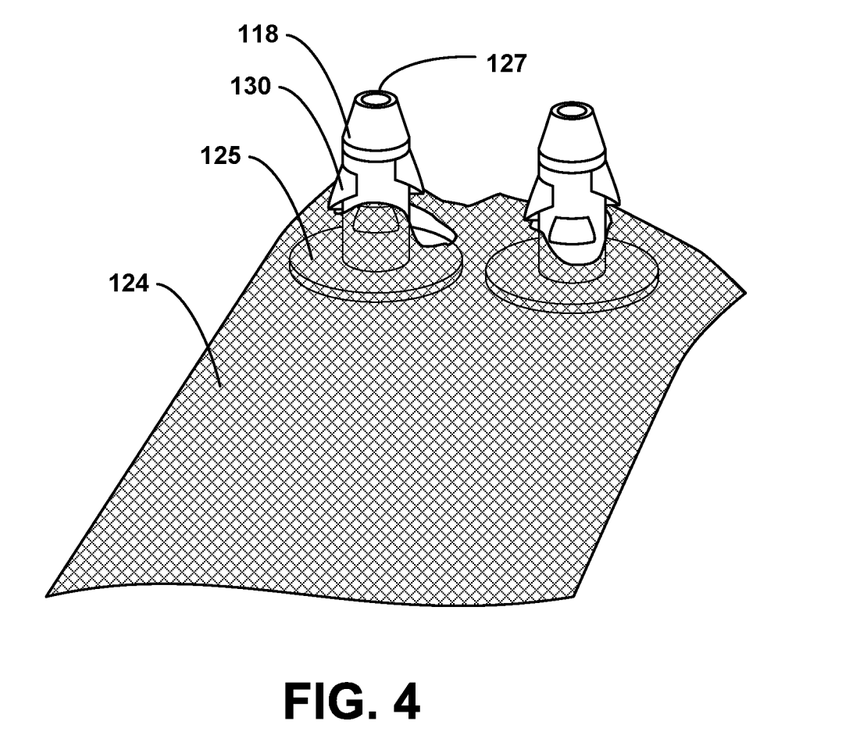
FIG. 4 is perspective view of a wound closure device with an example fixation component attached thereto, according to an example embodiment.

As discussed above, the wound closure device 116 may include at least two fixation components 118 connected thereto for affixing the wound closure device 116 to a tissue surface. Each fixation component 118 may include any device or structure capable of penetrating the tissue surface and securing the wound closure device 116 thereto. In one example, each fixation component 118 may be in the form of a staple-like device 126, as shown in FIG. 3A. Alternatively, each fixation component 118 may be a tack 128. The tack 128 may be provided in a number of various shapes and sizes, as shown in FIGS. 3B-3E. Other shapes are contemplated.

In one example, the tack 128 may have a central stem portion and a head or eyelet. In some embodiments, the tack 128 may include a pointed tip 127 to facilitate piercing of the tissue. Each of the tacks 128 may include one or more fins or protrusions 130 tapered radially outward to permit passage through the tissue and also to prevent the tacks from pulling or backing out of the tissue. The size, shape, material, and number and configuration of fins may provide a tack having a low insertion force and a high pullout force.

Figure 5:
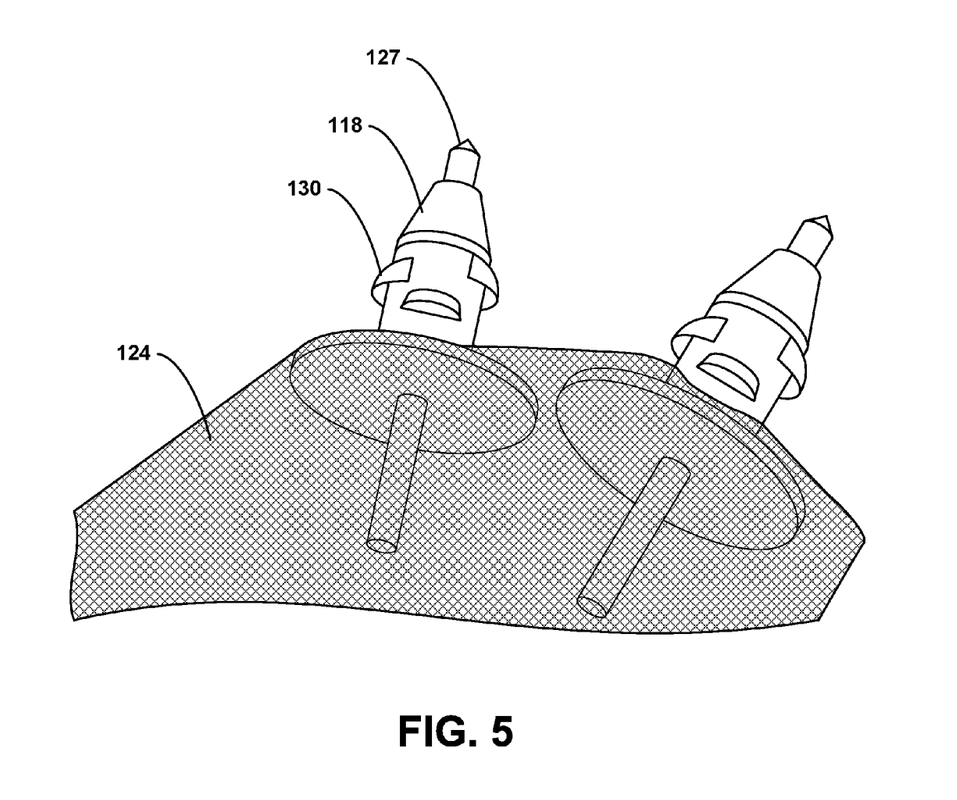
FIG. 5 is perspective view of a wound closure device with an example fixation component attached thereto, according to an example embodiment.
Figure 6:
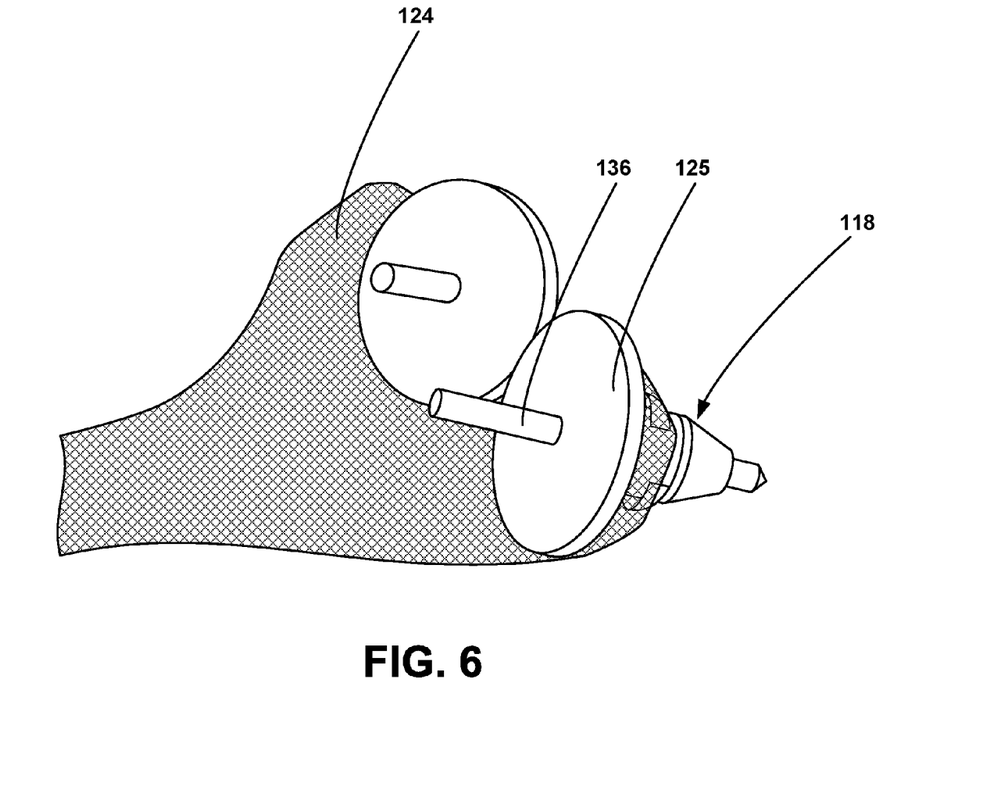
FIG. 6 is perspective view of a wound closure device with an example fixation component attached thereto, according to an example embodiment.
Figure 7:
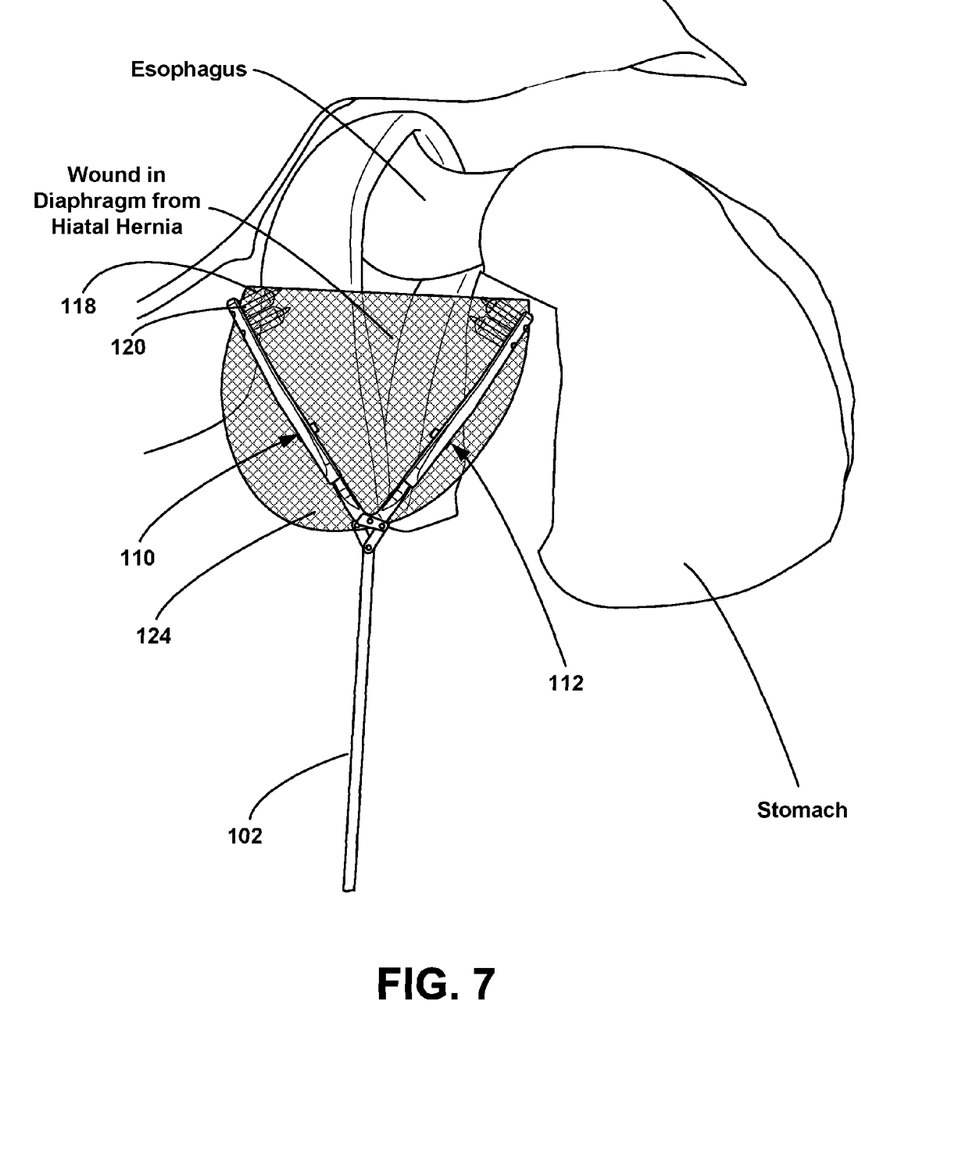
FIG. 7 illustrates an example deployment device positioning a wound closure device in a tissue, according to an example embodiment.

The fixation components 118 may be connected to the wound closure device 116, which may be a mesh 124, in any manner that will prevent the fixation components 118 from separating from the mesh. In one example, the fixation components 118 may be punctured through the mesh. In this manner, a flange 125 coupled to the fixation component 118 remains on one surface of the mesh, while the central stem of the fixation component 118 extends through the other surface, as shown in FIGS. 5-6. The eyelet of the fixation component 118 may act to stabilize it against the surface of the mesh. In some examples, the wound closure device 116 and fixation components 118 may be fabricated together such that the fixation components 118 and wound closure device 116 are formed as a continuous material. Alternatively, the fixation components 118 and wound closure device 116 may be fabricated separately, such that the fixation components 118 are subsequently secured to the wound closure device 116. In this case, the fixation components 118 and the wound closure device 116 may be formed from two different materials. Generally, the fixation components 118 may be formed from any suitable biocompatible materials, for example, resorbable poly (D, L)-lactide ("PLA").

In some examples, the wound closure device 116 may comprise at least two portions—an edge portion and a middle portion. The fixation components 118 may be connected to the edge portion. The middle portion may comprise a first material, and the edge portion may comprise a second material that is different than the first material. For example, the edge portion may be provided as a generally rigid and solid material to provide structural support for the fixation components 118, while the middle portion may comprise a mesh 124, as described above.

In one example, the at least one coupling element 120 of the first jaw 110 and the second jaw 112 is at least one pin configured to removably couple with the fixation component 118 connected to the wound closure device 116. The number of pins provided on each jaw 110, 112 may correspond to the number of fixation components 118 connected to the wound closure device 116. Accordingly, if the wound closure device 116 includes four fixation components 118, then each jaw 110, 112 of the grasping assembly 108 may be provided with two pins. Each fixation component 118 may, in some examples, include an axial hole 132 configured to accept a pin. Accordingly, the size of the axial hole 132 of the fixation component 118 may be sized and shaped to accommodate the size and shape of a pin, or vice versa. In some examples, the axial hole 132 of the fixation component 118 may extend from the flange 125 to the tip 127 of the fixation component 118, having an opening at both ends of the fixation component 118. The pin, in these examples, may have a length that is greater than the length of the fixation component 118, such that a portion of the pin extends beyond the tip 127 of the fixation component 118. Further, as the pin in this example is intended to pierce the tissue, it may include a sharp tip. In some examples, the tip of the pin may be pyramidal in shape, providing three cutting edges where each face joins. Alternatively, the axial hole 132 of each tack may not extend fully to the tip 127. In such cases, the end of the pin will remain concealed with the fixation component 118. As such, the tip 127 of the fixation component 118 will act to pierce the tissue and, therefore, the fixation component 118 may be provided with a tapered or pointed tip. In one example, the at least one pin extending from the first jaw 110 and the at least one pin extending from the second jaw 112 do not overlap when the grasping assembly is in the closed position, as shown in FIG. 2D.

In another example, the at least one coupling element 120 of the first jaw 110 and the second jaw 112 comprises a hole 134 configured to receive a pin 136 of a respective fixation component 118 connected to the wound closure device 116. Such an embodiment is shown in FIG. 6. In another example, the at least one coupling element 120 of the first jaw 110 and the second jaw 112 comprises a first magnet configured to attract a second magnet of a respective fixation component 118 connected to the wound closure device 116. Such an embodiment provides a temporary, removable connection between the wound closure device 116 and the grasping assembly 108.

In some embodiments, the grasping assembly 108 may come pre-loaded with a wound closure device 116 releasably attached thereto. The grasping assembly 108 may be disposable and removable from the rest of the deployment device 100.

In one example, the wound closure device 116 is provided with at least two fixation components 118, positioned such that at least one of the at least two tacks is inserted into the tissue surface on either side of the wound to be closed. Accordingly, each jaw 110, 112 of the grasping assembly 108 may be provided with at least one coupling element 120 configured to receive at least one fixation component 118 thereon. The deployment device 100 may also include a release mechanism for releasing the fixation components 118 from the coupling elements 120, once the fixation components 118 have been set in the intended tissue. In one example, where the coupling element 120 comprises a pin, the deployment device 100 may further include a catch or hook configured to retain a tack on the pin. The release mechanism, in this case, may be configured to withdraw the catch or hook, such that the tack may slide from the pin and be retained in the tissue. Mechanically, the release element may comprise a button or a lever. Other examples are contemplated.

As discussed above, an actuator 114 is coupled to the second end 106 of the elongate shaft 102, and is configured to move the grasping assembly 108 between an open position and a closed position. The actuator 114 need not be directly attached to the grasping assembly 108, but may be connected in an indirect manner with other elements in between them. In the closed position, the grasping assembly 108, with a wound closure device 116 coupled thereto, may be inserted into the body and brought into the vicinity of the wound to be closed. In the open position, the wound closure device 116 is exposed and the grasping assembly 108 may be used to bring the wound closure device 116 into abutment with the tissue surface. The actuator 114 may be any mechanism capable of moving the grasping assembly 108 between the open and closed positions. In one example, shown in FIG. 1, the actuator 114 may include a handle for grasping by a surgeon, including a stationary arm and a lever arm. The lever arm is coupled to a rod, which extends through the elongate shaft of the deployment device and is coupled to the grasping assembly at its distal end. Squeezing the handles of the actuator closed causes the rod to slide in the proximal direction and the jaws 110, 112 of the grasping assembly 108 to close. Opening the handles causes the jaws 110, 112 of the grasping assembly 108 to open. The handle may also be a ratcheting handle, as shown in FIG. 1, to lock the handle, and the grasping assembly in place. In further examples, the handle of the actuator 114 may be spring biased, such that the grasping assembly 108 is biased in a closed position. Other configurations and examples of the actuator 114 are contemplated.

In one example, each of the first jaw 110 and the second jaw 112 comprises a proximal jaw segment 138 (closest to the first end 104 of the elongate shaft 102) and a distal jaw segment 140. The distal jaw segment 140 may rotate with respect to the proximal jaw segment 138 at the hinge point, such that the distal jaw segment rotates 140 away from the closed position of the jaws. Each of the proximal jaw segment 138 and the distal jaw segment 140 may have approximately the same length. Other configurations are possible. The distal jaw segment 140 of each of the first and second jaws 110, 112 may be actuated independently of the proximal segment 138, and vice versa. Both the distal and proximal segments 138, 140 of each jaw 1102, 112 may be coupled to the same actuator 114. In use, operation of the actuator 114 may cause the proximal jaw segment 138 of each jaw to open to a maximum opening position. Once the proximal jaw segments 138 reach the maximum opening position, operation of the actuator 114 may then engage the distal jaw segments 140 and cause the distal jaw segments 140 to rotate. In another embodiment, both the distal and proximal jaw segments 138, 140 may be operated by separate actuators. For example, the actuator 114 may include two lever arms, one in communication with the distal jaw segments 140 and another in communication with the proximal jaw segments 138. In such a configuration, the jaws 110, 112 may be configured to open in a two-step phase, thereby allowing the jaws 110, 112 to open at a wider angle.

In one embodiment, the wound closure device 116 comprises at least two pins 136 positioned on a first side of the wound closure device 116, and the at least one coupling element 120 of the first jaw 110 and the second jaw 112 comprises a hole 134 configured to receive a respective pin 136 of the wound closure device 116. In such an embodiment, the second side of the wound closure device 116 may include an adhesive. The adhesive is positioned on the wound closure device 116 (e.g., the mesh 124) on the surface that is configured to contact the tissue surface. Once the deployment device 100 positions the wound closure device 116 is in the desired position, the adhesive material of the wound closure device 116 can thereby be brought into abutment with the intended tissue surface. In one example, the adhesive comprises a microreplicated mesh or includes a microreplicated surface, as discussed above in relation to the mesh 124.

In another embodiment, the wound closure device 116 comprises a first surface configured to at least partially contact the first jaw 110 and the second jaw 112 of the grasping assembly 108, and a second surface configured to contact the tissue surface. In such an example, the at least one coupling element 120 of the first jaw 110 and the second jaw 112 may comprise a first adhesive positioned between the first surface of the wound closure device 116 and a respective jaw 110, 112. The first adhesive may be coupled to the first jaw 110 and/or the second jaw 112, or the first adhesive may be coupled to the first surface of the wound closure device 116. The first adhesive provides a removable connection between the wound closure device 116 and the jaws 110, 112. As such, in such an embodiment no pins are required to hold the wound closure device 116 to the deployment device 100. The wound closure device 116 may further include a second adhesive positioned on the second surface of the wound closure device 116. Once the deployment device 100 positions the wound closure device 116 is in the desired position, the second adhesive material of the wound closure device 116 can thereby be brought into abutment with the intended tissue surface. The second adhesive may be stronger than the first adhesive, such that the wound closure device 116 remains in abutment with the intended tissue surface and is released from the jaws 110, 112. In one example, the first adhesive and/or the second adhesive comprises a microreplicated mesh or includes a microreplicated surface, as discussed above.

In yet another embodiment, the wound closure device 116 comprises at least two fixation components 118 connected to and extending therethrough that removably couple with at least one coupling element 120 positioned on each of two jaws 110, 112 of a grasping assembly 108 of the deployment device 100. In such an example, the at least one coupling element 120 of the first jaw 110 and the second jaw 112 may comprise an adhesive positioned between a respective fixation component 118 and a respective jaw 110, 112. The adhesive may be coupled to the first jaw 110 and/or the second jaw 112, or the adhesive may be coupled to the respective fixation component 118, for example the flange 125 of the fixation component 118. The adhesive provides a removable connection between the fixation components 118 and the jaws 110, 112. Once the deployment device 100 positions the wound closure device 116 is in the desired position, the wound closure device 116 can thereby be brought into abutment with the intended tissue surface so that the fixation components 118 pierce the tissue surface. The securing force of the fixation components 118 once they pierce the tissue surface may be stronger than the adhesive, such that the wound closure device 116 remains in abutment with the intended tissue surface and is released from the jaws 110, 112.

An example method for repairing a wound in a tissue using the deployment device 100 is provided. In particular, the method may be used to repair a hiatal hernia. The wound closure device 100 includes at least two fixation components 118 connected to and extending therethrough that couple with at least one coupling element 120 positioned on each of two jaws 110, 112 of a grasping assembly 108 of the deployment device 100. In operation, once the distal end of the deployment device 100 is inserted into the body, with the grasping assembly 108 in an open position, so as to expose the wound closure device 116, the wound closure device 116 is brought into abutment with a tissue surface at the location of a wound, such as a hiatal wound. Generally, at least one fixation component 118 is positioned on each side of the wound closure device 116. As such, the grasping assembly 108 will position the wound closure device 116 such that at least one fixation component 118 is positioned on either side of the wound. The wound closure device 116 is affixed to the tissue surface by bringing the grasping assembly 108 into a closed position around a portion of the tissue such that the at least two fixation components 118 pierce the tissue surface, thereby affixing the wound closure device 116 to the tissue surface.

In particular, an example method for closing a wound in a tissue surface may include (a) bringing a wound closure device 116 coupled to a deployment device 100 adjacent to the tissue surface, where the wound closure device 116 includes (i) at least two fixation components 118 connected to and extending therethrough, and wherein the deployment device 100 includes (i) an elongate shaft having 102 a first end 104 and a second end 106, (ii) a grasping assembly 108 coupled to the first end 104 of the elongate shaft 102, wherein the grasping assembling 108 includes a first jaw 110 and a second jaw 112 rotatable with respect to the elongate shaft, where the grasping assembly 108 is configured to accept a wound closure device between the first jaw 110 and the second jaw 112, and (iii) an actuator 114 coupled to the second end 106 of the elongate shaft 102, wherein the actuator 114 is configured to move the grasping assembly 108 between an open position and a closed position, (b) with the grasping assembly 108 in the open position, bringing the wound closure device into abutment with the tissue surface, and (c) bringing the grasping assembly 108 into the closed position around a portion of the tissue surface such that the at least two fixation components 118 pierce the tissue surface, thereby affixing the wound closure device 116 to the tissue surface.

In one embodiment, each of the first jaw 110 and the second jaw 112 include at least one coupling element 120 configured to be removably coupled to a respective fixation component when the wound closure device 116 is coupled to the grasping assembly 108. In another embodiment, the at least one coupling element of the first jaw 110 and the second jaw 112 includes at least two pins configured to removably couple with a respective fixation component 118 connected to the wound closure device 116. In yet another embodiment, bringing the grasping assembly 108 into the closed position around the portion of the tissue surface causes the at least two pins to pierce the surface tissue.

It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

The invention claimed is:

1. A deployment system, comprising:
   an elongate shaft having a first end and a second end;
   a grasping assembly coupled to the first end of the elongate shaft, wherein the grasping assembly includes a first jaw and a second jaw rotatable with respect to the elongate shaft;
   an actuator coupled to the second end of the elongate shaft, wherein the actuator is configured to move the grasping assembly between an open position and a closed position; and
   a wound closure device configured to be positioned between the first jaw and the second jaw, wherein the wound closure device comprises at least four fixation components connected to and extending therethrough, wherein each of the first jaw and the second jaw include at least two pins configured to be removably coupled to a respective fixation component when the wound closure device is coupled to the grasping assembly, and wherein the at least two pins extending from the first jaw and the at least two pins extending from the second jaw do not overlap when the grasping assembly is in the closed position.

2. The deployment system of claim 1, wherein the wound closure device includes a biocompatible mesh.

3. The deployment system of claim 2, wherein the biocompatible mesh comprises a microreplicated mesh.

4. The deployment system of claim 2, wherein the mesh comprises a multilayer mesh, wherein at least one layer of the multilayer mesh comprises a microreplicated material.

5. The deployment system of claim 1, wherein the fixation component comprises a tack connected to the wound closure device.

6. The deployment system of claim 1, wherein the fixation component comprises at least one protrusion configured to penetrate a tissue surface.

7. The deployment system of claim 6, wherein the at least one protrusion comprises at least one barb extending away from a body of the fixation component.

8. The deployment system of claim 1, wherein each pin is configured to be received in an axial hole extending through the fixation component.

9. The deployment system of claim 1, wherein each pin has a greater length than the fixation component, such that an end of the pin extends beyond an end of the fixation component when coupled thereto.

10. The deployment system of claim 9, wherein the end of the pin that extends beyond the end of the fixation component includes a tapered end configured to penetrate a tissue surface.

11. The deployment system of claim 10, wherein the tapered end includes three cutting edges.

12. The deployment system of claim 1, wherein the the first jaw and the second jaw each comprise a hole configured to receive a pin of a respective fixation component connected to the wound closure device.

13. The deployment system of claim 1, wherein the the first jaw and the second jaw each comprise a first magnet configured to attract a second magnet of a respective fixation component connected to the wound closure device.

14. The deployment system of claim 1, further comprising a release mechanism configured to release the fixation component coupled to the at least two pins on each of the first jaw and the second jaw when the wound closure device is coupled to the grasping assembly.

15. The deployment system of claim 1, wherein each of the first jaw and the second jaw rotate with respect to the other.

16. The deployment system of claim 1, wherein each of the first jaw and the second jaw comprises a proximal jaw segment and a distal jaw segment, wherein the distal jaw segment is rotatable with respect to the proximal jaw segment.

17. A method of closing a wound in a tissue surface, the method comprising:
   bringing the deployment system of claim 1 adjacent to the tissue surface;
   with the grasping assembly in the open position, bringing the wound closure device into abutment with the tissue surface,
   bringing the grasping assembly into the closed position around a portion of the tissue surface such that the at least two fixation components pierce the tissue surface, thereby affixing the wound closure device to the tissue surface.

18. The method of claim 17, wherein bringing the grasping assembly into the closed position around the portion of the tissue surface causes the at least two pins of each of the first jaw and the second jaw to pierce the surface tissue.

* * * * *